(12) United States Patent
Ryan

(10) Patent No.: US 11,045,350 B2
(45) Date of Patent: Jun. 29, 2021

(54) INFUSION SUPPORT DEVICE AND METHOD

(71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 131 days.

(21) Appl. No.: 15/109,387

(22) PCT Filed: Dec. 19, 2014

(86) PCT No.: PCT/US2014/071678
§ 371 (c)(1),
(2) Date: Jun. 30, 2016

(87) PCT Pub. No.: WO2015/102963
PCT Pub. Date: Jul. 9, 2015

(65) Prior Publication Data
US 2016/0324686 A1    Nov. 10, 2016

Related U.S. Application Data

(60) Provisional application No. 61/921,969, filed on Dec. 30, 2013.

(51) Int. Cl.
*A61F 9/00* (2006.01)
*A61M 5/14* (2006.01)

(52) U.S. Cl.
CPC .......... *A61F 9/0017* (2013.01); *A61M 5/1418* (2013.01); *A61M 2005/1416* (2013.01);
(Continued)

(58) Field of Classification Search
CPC ........ A61F 9/0026; A61F 9/0017; A61F 9/00; A61F 9/007; A61F 9/008; A61F 9/04;
(Continued)

(56) References Cited

U.S. PATENT DOCUMENTS 3,664,340 A     5/1972  Morgan
RE28,873 E  *  6/1976  Morgan ................ A61F 9/0017
                                                              604/298
(Continued)

FOREIGN PATENT DOCUMENTS

DE    102009032184 A1    1/2011
EP        2522318 A1    11/2012
(Continued)

OTHER PUBLICATIONS

International Application Serial No. PCT/US2014/071678, International Search Report dated Jun. 4, 2015, 5 pgs.
(Continued)

*Primary Examiner* — Brandy S Lee
*Assistant Examiner* — Hong-Van N Trinh
(74) *Attorney, Agent, or Firm* — Schwegman Lundberg & Woessner, P.A.

(57) ABSTRACT

An ophthalmic infusion support and associated methods are shown. Example infusion support devices include a base region, a support region, and a fastener. The fastener may take on the form of a c-shaped clip. When in use, the ophthalmic infusion support holds an infusion tube at an angle projecting away from a patient's eye.

11 Claims, 2 Drawing Sheets

(52) U.S. Cl.
CPC ............... *A61M 2209/088* (2013.01); *A61M 2210/0612* (2013.01)

(58) Field of Classification Search
CPC .......... A61F 2009/0052; A61F 9/00781; A61F 9/0008; A61F 9/0061; A61B 17/0231; A61M 2210/0612; A61M 2005/1416; A61M 2209/088; A61M 2210/06; A61H 35/02
See application file for complete search history.

(56) References Cited

U.S. PATENT DOCUMENTS

| | | | |
|---|---|---|---|
| 4,781,675 A | 11/1988 | White | |
| 4,834,727 A * | 5/1989 | Cope | A61B 17/0231 604/300 |
| 5,429,621 A | 7/1995 | Stahl | |
| 5,795,342 A * | 8/1998 | Shapiro | A61H 35/02 604/294 |
| 6,090,086 A | 7/2000 | Bolden | |
| 6,371,945 B1 | 4/2002 | Sherman | |
| 2001/0008961 A1* | 7/2001 | Hecker | A61F 9/007 604/117 |
| 2008/0033462 A1* | 2/2008 | Di Nardo | A61F 9/007 606/166 |
| 2010/0010452 A1* | 1/2010 | Paques | A61F 9/0017 604/192 |
| 2010/0241102 A1* | 9/2010 | Ma | A61F 9/0017 604/506 |
| 2014/0094752 A1* | 4/2014 | Hiles | A61F 9/0017 604/116 |

FOREIGN PATENT DOCUMENTS

| | | |
|---|---|---|
| WO | WO-0168016 A2 | 9/2001 |
| WO | WO-2015102963 A2 | 7/2015 |
| WO | WO-2015102963 A3 | 7/2015 |

OTHER PUBLICATIONS

International Application Serial No. PCT/US2014/071678, Invitation to Pay Additional Fees and Partial Search Report dated Mar. 19, 2015, 2 pgs.
International Application Serial No. PCT/US2014/071678, Written Opinion dated Jun. 4, 2015, 9 pgs.
European Application Serial No. 14876293.3, Extended European Search Report dated Aug. 25, 2017, 6 pgs.
European Application Serial No. 14876293.3, Response filed Mar. 3, 2017 to Communication pursuant to Rules 161(2) abd 162 EPC mailed Sep. 2, 2016, 8 pgs.
European Application Serial No. 14876293.3, Response filed Mar. 21, 2018 to Extended European Search Report dated Aug. 25, 2017, 15 pgs.

* cited by examiner

INFUSION SUPPORT DEVICE AND METHOD

CLAIM OF PRIORITY

This application is a U.S. National Stage Filing under 35 U.S.C. 371 from International Application No. PCT/US2014/071678, filed on Dec. 19, 2014, and published as WO 2015/102963 A2 on Jul. 9, 2015, which claims the benefit of priority under 35 U.S.C. § 119(e) to U.S. Provisional Patent Application Ser. No. 61/921,969, filed on Dec. 30, 2013, each of which is hereby incorporated by reference herein in its entirety.

TECHNICAL FIELD

This invention relates to devices and methods for ophthalmological procedures, such as an infusion procedure.

BACKGROUND

A number of ophthalmological procedures require the use of an infusion line. Infusion lines have weight, and in some cases, may tend to flex as they hang from their coupling location on a patient's eye. It is desirable to avoid kinking of the infusion line, which may restrict fluid flow.

DETAILED DESCRIPTION

Figure 1:
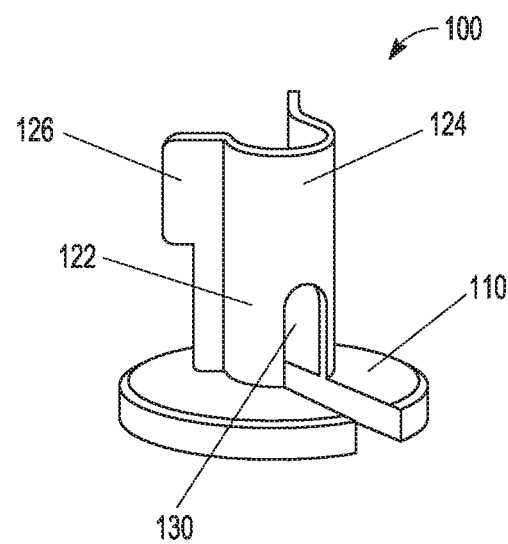
FIG. 1 shows an ophthalmic infusion support according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an ophthalmic infusion support 100 according to one example of the invention. The ophthalmic infusion support includes a base region 110 coupled to an infusion tube support region 122. The base region 110 is wider than the support region 122 in order to provide a level of increased support to an infusion tube. The base region 110 shown in FIG. 1 is approximately 2-3 times wider than a diameter of an infusion tube, although the invention is not so limited. Other diameters of a base region 110 may also be used, provided that the base region 110 provides supplementary support to the infusion tube when in use.

Although the term "diameter" is used to describe the base region 110, the base region 110 is not necessarily circular. Any number of shapes, including oval, rectangular, square, etc. may be used for the base region 110. In non-circular examples, the term "diameter" of the base region 110 refers to a diameter of a circle that would enclose the base region 110.

Figure 2:
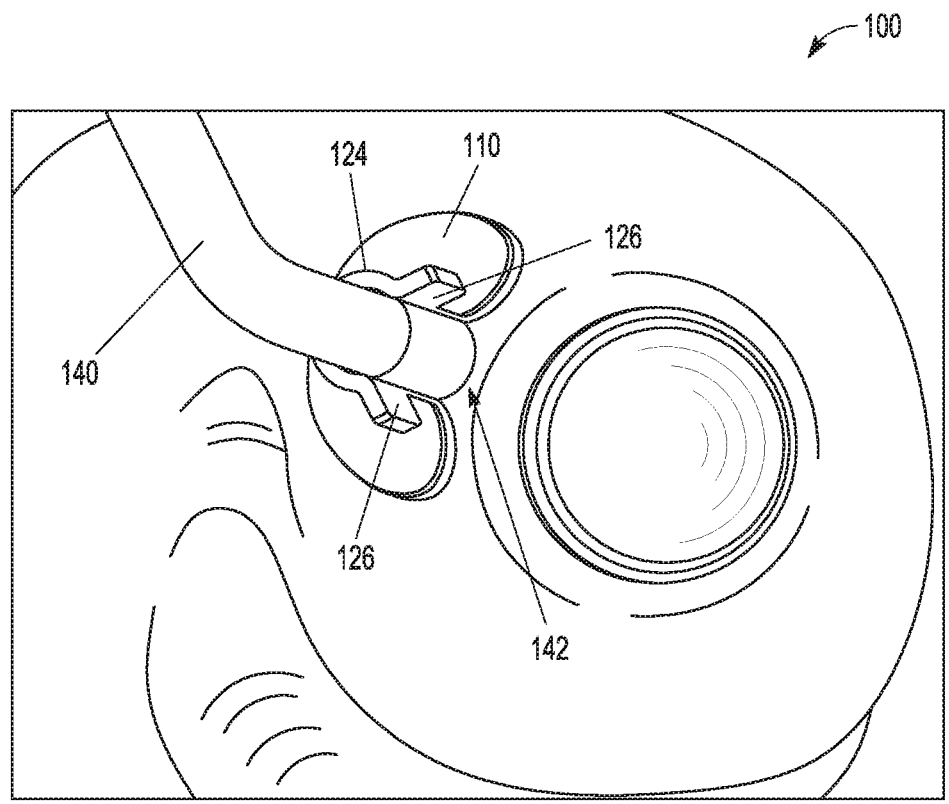
FIG. 2 shows an ophthalmic infusion support in a simulated use according to an embodiment of the invention.

A diameter of the base region 110 that is approximately 2-3 times wider than a diameter of an infusion tube is a useful dimension, and may provide an acceptable level of support, while still leaving a large portion of the patient's eye unobstructed by the base region 110. An example of the interaction of base region dimensions with a patient's eye is shown in FIG. 2.

In one example, the base region 110 includes a lower surface that includes a portion of a spherical curved surface. In one example, a radius of the spherical curved surface is chosen to substantially match a radius of curvature of a patient's eye. Examples of base regions 110 that include a spherical curved surface may further enhance support of the infusion tube by forming a more stable interface with the patient's eye.

The ophthalmic infusion support 100 shown in FIG. 1 also shows a fastener 124 that is adapted to couple to an infusion tube. In the example of FIG. 1, the fastener 124 includes a "C" shaped clip. In the example shown, the "C" shaped clip operates using a resilient material that flexes to allow insertion of the infusion tube, then returns to its original shape to hold the infusion tube. Other examples of fasteners may include a mechanical clasp, a fully encircling portion, an adhesive, a male and female mating fastener, etc. An advantage of the "C" shaped clip example shown includes ease of use and ease of manufacture.

In one example, the fastener 124 is formed from a polymeric material. Any suitable polymer that provides the desired flexibility and clamping force may be used. It is desirable to use materials that are biocompatible. Other example materials may include metal, such as titanium or stainless steel, etc.

In the example shown, the ophthalmic infusion support 100 is integrally formed. All components, including the base region 110, the infusion tube support region 122, and the fastener 124 may be integrally formed, for example, by injection molding. In other examples, different materials may be used to manufacture different components, and the ophthalmic infusion support 100 may be assembled from multiple parts. One advantage of integral forming includes ease of forming and reduced manufacturing cost.

One advantage of a polymer material includes the ability to form substantially transparent components. In one integrally formed example, the entire ophthalmic infusion support 100 is formed by injection molding a substantially transparent polymer. A transparent device is desirable because a surgeon will be able to better visualize the area of the procedure through at least a portion of the device.

The ophthalmic infusion support 100 shown in FIG. 1 also optionally includes a cut out 130. In one example, the addition of the cut out 130 provides additional flexibility to the ophthalmic infusion support 100, and in particular to the fastener 124. In one example the dimensions of the cut out 130, such as width, height, radius of top portion of the cut out 130, etc. may be varied to provide a desired level of flexibility and retention force for the fastener 124. In one example, the cut out 130 further provides visibility for a surgeon to see an end of a cannula, or other portion of an infusion tube that may protrude into the patient's eye.

The ophthalmic infusion support 100 shown in FIG. 1 also optionally includes a pair of guides 126. In one example, the guides 126 facilitate ease of coupling to the infusion tube by guiding the infusion tube to a center of the fastener 124 and aligning the infusion tube during a fastening operation.

FIG. 2 shows the ophthalmic infusion support 100 from FIG. 1 in a simulated use on a patient's eye. The infusion tube 140 is illustrated being supported at an orientation substantially normal to the base region. Although a normal angle is shown, other angles, such as 30 degrees, 60 degrees, 45 degrees, etc. with respect to a tangent of the patient's eye are also within the scope of the invention.

It can be seen from FIG. 2 that the base region 110 as positioned into contact with the patient's eye. In the example shown, the size of the base region 110 provides support, and does not block a surgeon's view of other major portions of the patient's eye. In the example shown, a base cut out 142 is included, and may be positioned adjacent to the iris of the patient's eye, to allow the surgeon a larger unobstructed view.

Figure 3:
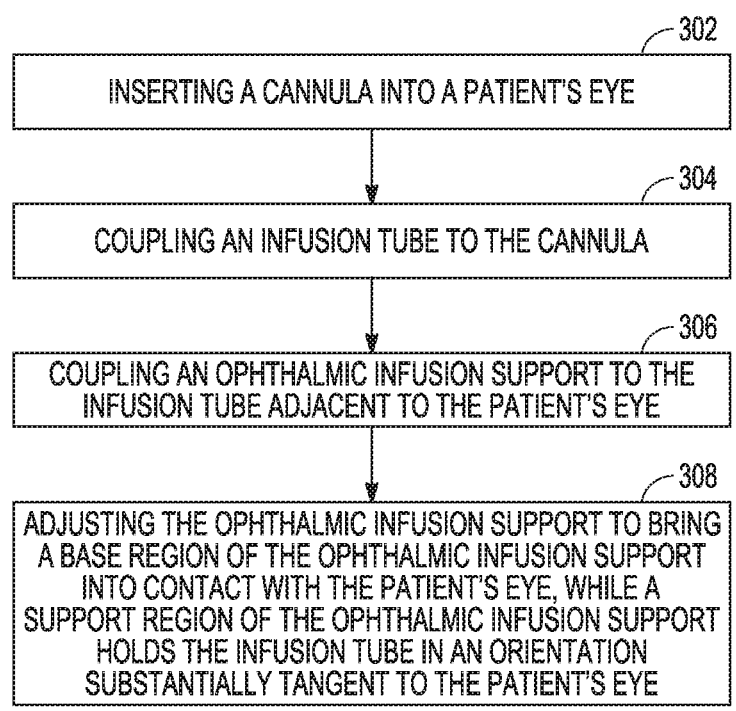
FIG. 3 shows an example method of using an ophthalmic infusion support according to an embodiment of the invention.

FIG. 3 shows a method of using an ophthalmic infusion support, such as the ophthalmic infusion support 100 described in examples above. In operation 302, a cannula is inserted into a patient's eye. In operation 304, an infusion tube is coupled to the cannula. In operation 306, an ophthalmic infusion support is coupled to the infusion tube adjacent to the patient's eye. In operation 308, the ophthalmic infusion support is adjusted to bring a base region of the ophthalmic infusion support into contact with the patient's eye, while a support region of the ophthalmic infusion support holds the infusion tube in an orientation substantially tangent to the patient's eye.

To better illustrate the method and apparatuses disclosed herein, a non-limiting list of embodiments is provided here:

Example 1 includes an ophthalmic infusion support. The ophthalmic infusion support includes a base region having a contact surface adapted for positioning against a patient's eye, an infusion tube support region extending from the base region, and a fastener to hold the ophthalmic infusion support to an infusion tube.

Example 2 includes the ophthalmic infusion support of example 1, wherein the base region includes a portion of a spherical curved surface, shaped to form a substantially continuous interface with a portion of the patient's eye.

Example 3 includes the ophthalmic infusion support of any one of examples 1-2, wherein the fastener is integral with the infusion tube support region.

Example 4 includes the ophthalmic infusion support of any one of examples 1-3, wherein the base region, the infusion tube support region and the fastener are integrally formed from a polymer material.

Example 5 includes the ophthalmic infusion support of any one of examples 1-4, wherein the fastener includes a "C" shaped clip, and wherein the "C" shaped clip also serves as the infusion tube support region.

Example 6 includes the ophthalmic infusion support of any one of examples 1-5, wherein the base region includes a cut out to enhance flexibility and operation of the fastener.

Example 7 includes the ophthalmic infusion support of any one of examples 1-6, wherein the cut out extends into the infusion tube support region.

Example 8 includes the ophthalmic infusion support of any one of examples 1-7, wherein the fastener couples to the infusion support tube directly adjacent to the patient's eye when in use.

Example 9 includes the ophthalmic infusion support of any one of examples 1-8, further including a pair of guides coupled to the fastener to facilitate coupling to the infusion tube.

Example 10 includes the ophthalmic infusion support of any one of examples 1-9, wherein the infusion tube support region is oriented substantially normal to the base region.

Example 11 includes a method that includes inserting a cannula into a patient's eye, coupling an infusion tube to the cannula, coupling an ophthalmic infusion support to the infusion tube adjacent to the patient's eye, and adjusting the ophthalmic infusion support to bring a base region of the ophthalmic infusion support into contact with the patient's eye, while a support region of the ophthalmic infusion support holds the infusion tube in an orientation substantially tangent to the patient's eye.

Example 12 includes the method of example 11, wherein coupling an ophthalmic infusion support to the infusion tube includes fastening a "C" shaped clip to the infusion tube.

Example 13 includes the method of any one of examples 11-12, wherein adjusting the ophthalmic infusion support to bring a base region of the ophthalmic infusion support into contact with the patient's eye includes adjusting a portion of a spherical curved surface into contact with the patient's eye, wherein the portion of a spherical curved surface substantially matches a curvature of the patient's eye.

These and other examples and features of the present electronic device, and related methods will be set forth in part in the above detailed description. This overview is intended to provide non-limiting examples of the present subject matter—it is not intended to provide an exclusive or exhaustive explanation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An ophthalmic infusion support system, comprising:
   a flexible infusion tube;
   an ophthalmic infusion support, including;
   a base region having a contact surface adapted for positioning the entire contact surface against a patient's eyeball;
   an infusion tube support region, connected to, and extending from the base region wherein the contact surface is wider than an outer diameter of the infusion tube; and
   a fastener including a "C" shaped dip to hold the ophthalmic infusion support to the infusion tube, the fastener configured to be fastened to the infusion tube after an infusion cannula is inserted into the patient's eyeball, and wherein the "C" shaped dip also serves as the infusion tube support region.

2. The ophthalmic infusion support system of claim 1, wherein the base region includes a portion of a spherical curved surface, shaped to form a substantially continuous interface with a portion of the patient's eyeball.

3. The ophthalmic infusion support system of claim 1, wherein the fastener is integral with the infusion tube support region.

4. The ophthalmic infusion support system of claim 1, wherein the base region, the infusion tube support region and the fastener are integrally formed from a polymer material.

5. The ophthalmic infusion support system of claim 1, wherein the base region includes a cut out to enhance flexibility and operation of the fastener.

6. The ophthalmic infusion support system of claim 5, wherein the cut out extends into the infusion tube support region.

7. The ophthalmic infusion support system of claim 1, wherein the fastener couples to the infusion tube directly adjacent to the patient's eyeball when in use.

8. The ophthalmic infusion support system of claim 1, further including a pair of guides coupled to the fastener to facilitate coupling to the infusion tube.

9. The ophthalmic infusion support system of claim 1, wherein the infusion tube support region is oriented substantially normal to the base region.

10. A method, comprising:
    inserting a cannula into a patient's eye;
    coupling a flexible infusion tube to the cannula;
    coupling a "C" shaped clip of an ophthalmic infusion support to the infusion tube adjacent to the patient's eye after the infusion tube is coupled to the cannula; and
    adjusting the ophthalmic infusion support to bring a base region of the ophthalmic infusion support into contact with the patient's eye, wherein a contact surface of the base region is wider than an outer diameter of the infusion tube, and wherein a support region of the ophthalmic infusion support holds the infusion tube in an orientation substantially tangent to the patient's eye.

11. The method of claim 10, wherein adjusting the ophthalmic infusion support to bring the base region of the ophthalmic infusion support into contact with the patient's eye includes adjusting a portion of a spherical curved surface into contact with the patient's eye, wherein the portion of the spherical curved surface substantially matches a curvature of the patient's eye.

* * * * *